US012617823B2

(12) United States Patent
Ye et al.

(10) Patent No.: US 12,617,823 B2
(45) Date of Patent: May 5, 2026

(54) BROAD-SPECTRUM PEPTIDE ANTIGEN OF THE NOVEL CORONAVIRUS SARS-COV-2, SPECIFIC NEUTRALIZING ANTIBODY AND USE THEREOF

(71) Applicant: YANGZHOU UNIVERSITY, Jiangsu (CN)

(72) Inventors: Jianqiang Ye, Jiangsu (CN); Tuofan Li, Jiangsu (CN); Qiuqi Kan, Jiangsu (CN); Aijian Qin, Jiangsu (CN); Zhimin Wan, Jiangsu (CN); Hongxia Shao, Jiangsu (CN); Quan Xie, Jiangsu (CN)

(73) Assignee: Yangzhou University, Jiangsu (CN)

( * ) Notice: Subject to any disclaimer, the term of this patent is extended or adjusted under 35 U.S.C. 154(b) by 243 days.

(21) Appl. No.: 17/620,528

(22) PCT Filed: Jul. 21, 2021

(86) PCT No.: PCT/CN2021/107615
§ 371 (c)(1),
(2) Date: Dec. 15, 2022

(87) PCT Pub. No.: WO2022/257237
PCT Pub. Date: Dec. 15, 2022

(65) Prior Publication Data
US 2024/0002451 A1     Jan. 4, 2024

(30) Foreign Application Priority Data

Jun. 7, 2021    (CN) ......................... 202110631147.0

(51) Int. Cl.
| | |
|---|---|
| C07K 14/165 | (2006.01) |
| A61P 31/14 | (2006.01) |
| C07K 14/005 | (2006.01) |
| C12N 15/10 | (2006.01) |
| G01N 33/68 | (2006.01) |

(52) U.S. Cl.
CPC .......... C07K 14/165 (2013.01); C07K 14/005 (2013.01); C12N 15/10 (2013.01); G01N 33/6854 (2013.01); A61P 31/14 (2018.01); C07K 2319/00 (2013.01); G01N 2333/165 (2013.01)

(58) Field of Classification Search
CPC ......................... C07K 14/165; C07K 14/005; C07K 2319/00; C12N 15/10; G01N 33/6854; G01N 2333/165; A61P 31/14
See application file for complete search history.

(56) References Cited

U.S. PATENT DOCUMENTS

| | | | | |
|---|---|---|---|---|
| 10,906,944 B2 * | 2/2021 | He | ......................... | A61P 31/14 |
| 2007/0092936 A1 * | 4/2007 | Haynes | ............... | C07K 14/005 |
| | | | | 435/5 |
| 2020/0407402 A1 * | 12/2020 | He | ......................... | A61K 39/12 |

FOREIGN PATENT DOCUMENTS

| | | |
|---|---|---|
| CN | 111217919 A | 6/2020 |
| CN | 111848753 A | 10/2020 |
| CN | 112409496 A | 2/2021 |
| CN | 112535730 A | 3/2021 |
| CN | 113444154 A | 9/2021 |
| CN | 113461787 A | 10/2021 |

OTHER PUBLICATIONS

Richmond P, et al. "Safety and immunogenicity of S-Trimer (SCB-2019), a protein subunit vaccine candidate for COVID-19 in healthy adults: a phase 1, randomised, double-blind, placebo-controlled trial." The Lancet, Feb. 20, 2021; 397(10275):682-94; doi: 10.1016/S0140-6736(21)00241-5 (Year: 2021).*
ZHENG, ZQ 4 Monoclonal antibodies for the S2 subunit of spike of SARS-CoV-1 cross-react with the newly-emerged SARS-CoV-2 Euro Surveill, (July 167, 2020) pp. 19-28.
NCBI GenBank accession No. QHD43416.1 NCBI GenBank (Mar. 18, 2020).
International Search Report dated Feb. 15, 2022.

* cited by examiner

*Primary Examiner* — Anand U Desai
*Assistant Examiner* — Andrew T Moehlman
(74) *Attorney, Agent, or Firm* — Aasheesh Shravah; CM Law LLP

(57)         ABSTRACT

The present disclosure provides a broad-spectrum peptide antigen of SARS-COV-2, a specific neutralizing antibody and use thereof. A broad-spectrum peptide antigen of SARS-COV-2, with an amino acid sequence comprising SEQ ID NO: 1, reacts with human SARS-COV-2 positive serum, and can specifically bind to a novel coronavirus antibody. Based on the peptide sequence of the present disclosure, a fusion protein with broad-spectrum triple tandem peptides of SARS-COV-2 is prepared using PCR, prokaryotic expression, and protein purification technology which simulates the trimeric mode of SARS-COV-2 S protein in its natural state. The fusion protein is used as an antigen to immunize mice, and can produce a specific anti-SARS-CoV-2 neutralizing antibody. The neutralizing antibody may be promising in anti-infective treatment, vaccine development and detection kit development for SARS-COV-2.

1 Claim, 4 Drawing Sheets

Specification includes a Sequence Listing.

M    1    2    3

3×P4 Protein pc-SARS-CoV-2-S                              pc

BROAD-SPECTRUM PEPTIDE ANTIGEN OF THE NOVEL CORONAVIRUS SARS-COV-2, SPECIFIC NEUTRALIZING ANTIBODY AND USE THEREOF

CROSS REFERENCE TO RELATED APPLICATION

This patent application is a National Stage application that claims the benefit and priority to International Application No. PCT/CN2021/107615, filed on Jul. 21, 2021, entitled "BROAD-SPECTRUM PEPTIDE ANTIGEN OF THE NOVEL CORONAVIRUS SARS-COV-2, SPECIFIC NEU-TRALIZING ANTIBODY AND USE THEREOF", which claims the benefit of and priority to Chinese Patent Appli-cation No. 202110631147.0 filed on Jun. 7, 2021, the disclosures of which is are incorporated by reference herein in their its entirety as part of the present application.

TECHNICAL FIELD

The present disclosure belongs to the technical filed of immunoassay of virus, and particularly relates to a broad-spectrum peptide antigen of the novel coronavirus SARS-CoV-2, a specific neutralizing antibody and use thereof.

BACKGROUND ART

The novel coronavirus SARS-CoV-2 is a highly infectious virus. The S protein of SARS-CoV-2 includes two subunits, i.e. S1 and S2. The S1 subunit binds to the cell receptor angiotensin-converting enzyme 2 (ACE2) via its receptor binding domain (RBD), and the S2 subunit mediates the fusion between the virus and the cell membrane through a fusion peptide (FP). Due to the important role in the fusion process during infection, S2 can be used as a target for extensive protection. At present, the frequent emergence of SARS-CoV-2 escape mutants has brought challenges to current immunologically advantageous strategy of receptor-binding-domain (RBD)-based vaccine against SARS-CoV-2.

However, there are currently no broad-spectrum vaccine against SARS-CoV-2 and rapid detection method for detect-ing anti-S2 antibodies.

SUMMARY

In view of this, the objective of the present disclosure is to provide a broad-spectrum peptide antigen of SARS-CoV-2. The antigen shows no mutation in the SARS-CoV-2 prototype strain and various epidemic mutant strains, is capable of specifically identifying the antibody to SARS-CoV-2 and has good antigenicity.

The present disclosure provides a broad-spectrum peptide antigen of SARS-CoV-2, in which the amino acid sequence of the broad-spectrum peptide antigen is set forth in SEQ ID NO: 1.

The present disclosure provides a fusion protein having broad-spectrum triple tandem peptides for SARS-CoV-2, in which the fusion protein includes three tandemly arranged sequences of the broad-spectrum peptide antigen of SARS-CoV-2.

Preferably, the amino acid sequence of the fusion protein is set forth in SEQ ID NO: 8.

The present disclosure provides a generation method of the fusion protein having broad-spectrum triple tandem peptides for SARS-CoV-2, including the following steps:

1) performing PCR amplification with a primer pair having nucleotide sequences set forth in SEQ ID NO: 6 and SEQ ID NO: 7 using plasmid pCold I as template to obtain a linearized pCold I expression vector;

2) amplifying a first fragment by PCR with a primer pair as set forth in SEQ ID NO: 2 and SEQ ID NO: 3, amplifying a second fragment by PCR with a primer pair as set forth in SEQ ID NO: 4 and SEQ ID NO: 3, and amplifying a third fragment by PCR with a primer pair as set forth in SEQ ID NO: 4 and SEQ ID NO: 5, using plasmid pcDNA3.1-SARS-CoV-2-S as template;

3) performing rapid recombinant cloning of linearized pCold I expression vector in step 1) and the first fragment, the second fragment and the third fragment in step 2) with a recombinase to obtain a recombinant plasmid; and 4) transforming cells with the recombinant plasmid in step 3), generating a fusion protein through cell culture and IPTG induction.

Preferably, an amplification procedure of the PCR in step 2) includes denaturation at 94° C. for 5 min, 30 cycles of denaturation at 94° C. for 30 s, annealing at 57° C. for 30 s and extension at 72° C. for 3 min and a final extension at 72° C. for 10 min.

An amplification reaction system for the PCR includes 33 µl water, 10 µl of 5× buffer, 1 µl of 10 mM dNTP, 2 µl of 10 µM upstream primer, 2 µl of 10 µM downstream primer, 1 µl of 10 ng/µl pCold I plasmid or pcDNA3.1-SARS-CoV-2-S plasmid, and 1 µl of commercial Phanta Super-Fidelity DNA polymerase.

The present disclosure provides the use of the broad-spectrum peptide antigen of SARS-CoV-2 and a fusion protein having broad-spectrum triple tandem peptides for novel coronavirus SARS-CoV-2 in preparing a broad-spec-trum subunit vaccine against SARS-CoV-2 and/or a kit for immunoassay of S2 antibody to novel coronavirus SARS-CoV-2.

Preferably, the immunoassay includes colloidal gold immunoassay, immunoprecipitation, fluorescence immuno-assay and/or enzyme-linked immunoassay.

The present disclosure provides an ELISA kit for detect-ing an antibody to SARS-CoV-2, including an ELISA plate coated with an antigen; the antigen includes the broad-spectrum peptide antigen of SARS-CoV-2 or the fusion protein having broad-spectrum triple tandem peptides of SARS-CoV-2.

The present disclosure provides a broad-spectrum neu-tralizing antibody to novel coronavirus SARS-CoV-2, in which the antibody is generated by immunizing an animal using the fusion protein with broad-spectrum triple tandem peptides for novel coronavirus SARS-CoV-2 or the fusion protein having broad-spectrum triple tandem peptides for SARS-CoV-2 generated by the generation method.

The present disclosure provides a medicine for preventing and/or treating SARS-CoV-2, and the medicine includes the broad-spectrum neutralizing antibody to SARS-CoV-2.

The broad-spectrum peptide antigen of SARS-CoV-2 provided in the present disclosure has an amino acid sequence set forth in SEQ ID NO: 1. The peptide antigen provided in the present disclosure is synthesized based on the peptide sequence of the S2 subunit of the SARS-CoV-2 S gene with good antigenicity. The antigen shows no muta-tion in the SARS-CoV-2 prototype strain and various epi-demic mutant strains, and has the identical amino acid sequence in other coronaviruses including SARS-CoV and BatCoV RaTG13, thus having excellent broad-spectrum antigen performance. The present disclosure confirms that the peptide has strong specificity by measuring the reaction between the antigen and the serum from COVID-19 recovered patients. The antigen takes advantage of the peptide antigen and may be applied to detection of the antibodies against SARS-CoV-2 S2. Compared with other methods, this method has the advantages of being fast, safe, reliable, and highly workable. The use of a peptide antigen as specific antibody in antigen detection samples makes the preparation of kits and sample detection more rapid and simple, and is an evaluation indicator for levels of broad-spectrum antibody in immunized populations or SARS-CoV-2 patients.

The present disclosure also provides a fusion protein having broad-spectrum triple tandem peptides for SARS-CoV-2. The fusion protein includes three tandemly arranged sequences of the broad-spectrum peptide antigen of SARS-CoV-2. The fusion protein not only increases the amount of antigen expression and lays a foundation for practical large-scale production, but also simulates the natural state of SARS-CoV-2 S protein at the time of infection, which has the characteristics of a trimer. Simultaneously, application of the fusion protein having broad-spectrum peptides for SARS-CoV-2 prepared in the present disclosure to immunize an animal may produce a specific neutralizing antibody to anti-SARS-CoV-2 broad-spectrum, which lays solid foundation for the development of broad-spectrum vaccines against SARS-CoV-2.

The present disclosure also provides a broad-spectrum neutralizing antibody against SARS-CoV-2, which is produced by immunizing an animal using the fusion protein having broad-spectrum triple tandem peptides for SARS-CoV-2. The broad-spectrum neutralizing antibody is capable of specifically binding to the antigen site of SARS-CoV-2, thereby blocking the occurrence and development of, providing a new idea for the prevention and treatment of.

DETAILED DESCRIPTION OF THE EMBODIMENTS

Figures 1, 2:
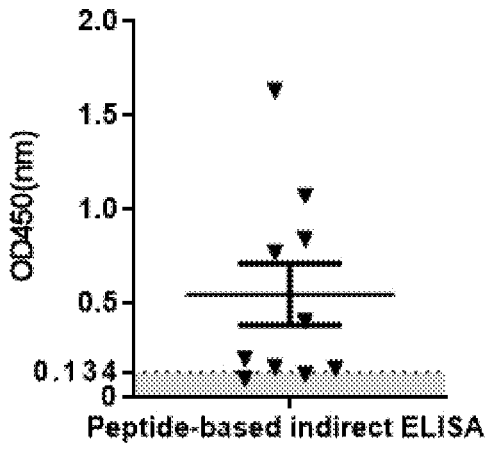
FIG. 1 shows the results for the detection of positive serum from COVID-19 recovered patients by ELISA using a coated peptide antigen.
FIG. 2 is an electrophoresis diagram of the 3 corresponding gene fragments of SEQ ID NO: 1 amplified by PCR, in which lane 1 is the first fragment; lane 2 is the second fragment; lane 3 is the third fragment; and lane M is DNA Marker.

The present disclosure provides a broad-spectrum peptide antigen for SARS-CoV-2, and the broad-spectrum peptide antigen has the amino acid sequence set forth in SEQ ID NO: 1 (DPLQPELDSFKEELDKYFKNHT-SPDVDLGDIS). The peptide antigen shows no mutation in the SARS-CoV-2 prototype strain and various epidemic mutant strains and has identical amino acid sequence in other coronaviruses (SARS-CoV and BatCoV RaTG13). And through the reaction with human SARS-CoV-2 positive sera, the specificity of the peptide antigen is confirmed. Therefore, based on the peptide antigen, a simple and quick ELISA is established to specifically detect SARS-CoV-2 antibody (S2 antibody).

The present disclosure provides a fusion protein having broad-spectrum triple tandem peptides for SARS-COV-2. The fusion protein includes three tandemly arranged sequences of the broad-spectrum peptide antigen for SARS-COV-2. The fusion protein preferably has a connecting peptide between the broad-spectrum peptide antigens of SARS-COV-2. The amino acid sequence of the connecting peptide is not particularly limited, and amino acid sequences of the connecting peptides well known in the art can be used. In an embodiment of the present disclosure, the amino acid sequence of the connecting peptide is GGGGS (SEQ ID NO: 9). The amino acid sequence of the fusion protein is preferably the sequence as set forth in SEQ ID NO: 8 HHHHHHIEGRHMELGTDPLQPELDSF-KEELDKYFKNHTSPDVDLGDISGGGGSDPLQPE LDSFKEELDKYFKNHTSPDVDLGDIS-GGGGSDPLQPELDSFKEELDKYFKNHTSPDVDL GDISKLVDLQSR. The 5'-end of the fusion protein contains a histidine tag, facilitating subsequent isolation and purification. The fusion protein can mimic the trimer mode of the S protein of SARS-COV-2 in natural state. Immunizing mice with the fusion protein as an antigen could produce a specific neutralizing antibody to SARS-COV-2.

The present disclosure provides a generation method of the fusion protein having broad-spectrum triple tandem peptides for SARS-CoV-2, including the following steps:

1) performing PCR amplification with a primer pair that has nucleotide sequences set forth in SEQ ID NO: 6 and SEQ ID NO: 7 to obtain a linearized pCold I expression vector, using a pCold I plasmid as template;

2) amplifying a first fragment by PCR with nucleotide sequences including a primer pair as set forth in SEQ ID NO: 2 and SEQ ID NO: 3, amplifying a second fragment by PCR with nucleotide sequences including a primer pair as set forth in SEQ ID NO: 4 and SEQ ID NO: 3, and amplifying a third fragment by PCR with a primer pair set forth in SEQ ID NO: 4 and SEQ ID NO: 5, using a pcDNA3.1-SARS-CoV-2-S plasmid as template;

3) performing rapid recombinant cloning of the linearized pCold I expression vector in step 1) and the first fragment, the second fragment and the third fragment in step 2) with a recombinase to obtain a recombinant plasmid; and 4) transforming cells with the recombinant plasmid in step 3), generating a fusion protein through cell culture and IPTG induction.

In the present disclosure, plasmid pCold I is used as a template, and the primer pair having nucleotide sequences set forth in SEQ ID NO: 6 (AAGCTTGTCGACCTGCAGTCTAGAT) and SEQ ID NO: 7 (GGTACCGAGCTCCATATGCCTACC) is used for PCR amplification to obtain the linearized pCold I expression vector.

The present disclosure does not impose special limitations on the source of the plasmid pCold I, and any source of the plasmid pCold I well known in the art can be used. In an embodiment of the present disclosure, the plasmid pCold I is purchased from Takara commercial plasmid (Takara Bio Inc. (Dalian)). The amplification procedure of the PCR preferably includes denaturation at 94° C. for 5 min, 30 cycles of denaturation at 94° C. for 30 s, annealing at 57° C. for 30 s and extension at 72° C. for 3 min and a final extension at 72° C. for 10 min. The reaction system for the PCR amplification preferably includes 33 μl of water, 10 μl of 5× buffer, 1 μl of 10 mM dNTP, 2 μl of 10 μM upstream primer, 2 μl of 10 μM downstream primer, 1 μl of 10 ng/μpCold I plasmid or pcDNA3.1-SARS-CoV-2-S plasmid, and 1 μl of commercial Phanta Super-Fidelity DNA polymerase.

In the present disclosure, the plasmid pcDNA3.1-SARS-CoV-2-S is used as a template, and the primer pair as set forth in SEQ ID NO: 2 and SEQ ID NO: 3 is used to amplify the first fragment by PCR; the primer pair as set forth in SEQ ID NO: 4 and SEQ ID NO: 3 is used to amplify the second fragment by PCR, and the primer pair as set forth in SEQ ID NO: 4 and SEQ ID NO: 5 is used to amplify the third fragment by PCR.

In the present disclosure, the plasmid pcDNA3.1-SARS-CoV-2-S is purchased from Shanghai HedgehogBio Science Co., Ltd. The primer pair for amplifying the first fragment includes a primer as set forth in SEQ ID NO: 2 (ATG-GAGCTCGGTACCGACCCATTGCAACCCGAACTTG) and a primer as set forth in SEQ ID NO: 3 (ACTTC-CACCTCCACCGCTAATGTCGCCCAGGTCCAC). The primer pair for amplifying the second fragment preferably includes a primer as set forth in SEQ ID NO: 4 (GGTG-GAGGTGGAAGTGACCCATTGCAACCCGAACTTG) and in SEQ ID NO: 3. The primer pair for amplifying the third fragment includes a primer as set forth in SEQ ID NO: 4 and a primer as set forth in SEQ ID NO: 5 (CAGGTCGACAAGCTTTCAGCTAATGTCGCCCA-GGTCCAC).

In the present disclosure, amplification procedure for the PCR of the first fragment, the second fragment and the third fragment preferably includes denaturation at 94° C. for 5 min, 30 cycles of denaturation at 94° C. for 30 s, annealing at 57° C. for 30 s and extension at 72° C. for 3 min and a final extension at 72° C. for 10 min. The reaction system for the PCR amplification preferably includes 33 μl of water, 10 μl of 5× buffer, 1 μl of 10 mM dNTP, 2 μl of 10 μM upstream primer, 2 μl of 10 μM downstream primer, 1 μl of 10 ng/μl plasmid pCold I or plasmid pcDNA3.1-SARS-CoV-2-S, and 1 μl of commercial Phanta Super-Fidelity DNA polymerase.

In the present disclosure, after the linearized pCold I expression vector, the first fragment, the second fragment and the third fragment are obtained, recombinase is used to perform rapid recombinant cloning of the linearized expression vector pCold I, the first fragment, the second fragment and the third fragment to obtain a recombinant plasmid.

In the present disclosure, the recombinase is preferably ClonExpress® MultiS One Step Cloning Kit. The recombinant cloning system includes 2 μl of linearized vector (containing 100 ng), 1 μl of each of the first fragment, the second fragment and the third fragment (containing 10 ng each), 4 μl of CE MultiS Buffer, 2 μl of Exnase MultiS, and 9 μl of water. The reaction procedure of the recombinant cloning is conducted at 37° C. for 30 minutes, temperature decreased to 4° C. 10004611n the present disclosure, after the recombinant plasmid is obtained, identification of the positive recombinant plasmid is preferably carried out. The method for the identification preferably includes transforming the recombinant plasmid into conventional DH5α competent bacteria, coating LB plates, picking bacterial clones the next day, performing PCR, detecting positive clones to obtain positive bacteria, and extracting plasmids to obtain positive recombinant plasmids.

After the identification, the recombinant plasmids are transformed into cells, and the fusion protein is obtained through cell culture and IPTG induction.

The transforming method is not limited to those in the present disclosure, and transforming methods well known in the art can be adopted. After the transformation, identification of positive clone is preferably performed on the transformed cells, and 3 peptide antigen fragments are obtained by PCR amplification, indicating that the transformation is successful. The identified positive clones are cultured and induced by IPTG to obtain cells expressing the fusion protein. The cell type is preferably BL21 competent bacteria.

After the cells expressing the fusion protein are obtained, the fusion protein is preferably isolated and purified. The isolation and purification methods are not particularly limited, and isolation and purification methods well known in the art can be used.

Given that the peptide antigen is highly conserved in a variety of coronaviruses including SARS-CoV-2, and has excellent antigenicity, the present disclosure provides the use of the broad-spectrum peptide antigen for SARS-CoV-2 and the fusion protein having broad-spectrum triple tandem peptides for SARS-CoV-2 in preparing a broad-spectrum subunit vaccine against SARS-CoV-2 and/or a kit for immunoassay of S2 antibody to SARS-CoV-2. The immunoassay may include colloidal gold immunoassay, immunoprecipitation, fluorescence immunoassay and/or enzyme-linked immunoassay.

The present disclosure provides an ELISA kit for detecting an antibody to SARS-CoV-2, including an ELISA plate coated with an antigen; the antigen may include the broad-spectrum peptide antigen of SARS-CoV-2 or the fusion protein having broad-spectrum triple tandem peptides for SARS-CoV-2.

In the present disclosure, the ELISA kit includes an enzyme-labeled antibody, a substrate solution, a stop solution, a washing solution, a negative control and a positive control. The enzyme-labeled antibody is horseradish peroxidase-labeled mouse anti-human IgG. The substrate solution is a solution obtained by mixing citric acid solution with $Na_2HPO_4 \cdot 12H_2O$ and adding tetramethylbenzidine. The preparation method of the substrate solution is preferably as follows: 24.3 mL of 100 mmol/L citric acid solution (21 g citric acid is dissolved in deionized water and made up to 1 L) and 25.7 mL of 200 mmol/L $Na_2HPO_4 \cdot 12H_2O$ (71.6 g $Na_2HPO_4 \cdot 12H_2O$ is dissolved in deionized water and made up to 1 L) were mix well, then 50 mg of tetramethylbenzidine (TMB) was added, and 50 μL of 30% $H_2O_2$ was added just before use. The stop solution was a 2M $H_2SO_4$ aqueous solution. The washing solution was preferably a 10 mmol/L PBS solution (pH 7.4) containing 5% Tween-20. The negative control was negative human serum. The positive control was mouse anti-SARS-CoV-2 serum.

In the present disclosure, the ELISA kit is prepared based on the capture method. In the present disclosure, the method for using the kit is not particularly limited and a method for using a capture ELISA kit well known in the art can be used.

The present disclosure provides a broad-spectrum neutralizing antibody to SARS-CoV-2 by immunizing an animal using the fusion protein having broad-spectrum triple tandem peptides for SARS-CoV-2 or the fusion protein having broad-spectrum triple tandem peptides for SARS-CoV-2 generated by the generation method. The animal preferably includes mice. The immunization is preferably performed twice. The interval between two immunizations is preferably 15 days. Experiments showed that the antibody prepared in the present disclosure can not only effectively recognized S protein of SARS-CoV-2, but also effectively neutralized SARS-CoV-2 S protein pseudovirus, and inhibited the viral entry into 293T cells stably expressing human ACE2. In other words, it is a broad-spectrum neutralizing antibody of SARS-CoV-2.

Given that the neutralizing antibody prevents viruses from invading eukaryotic cells, the present disclosure provides a medicine for preventing and/or treating SARS-CoV-2, and the medicine includes the broad-spectrum neutralizing antibody to SARS-CoV-2. In the present disclosure, the dosage form and preparation method of the medicine, a dosage form and preparation method of antibody medicines well known in the art can be used.

The following examples provide detailed description of the broad-spectrum peptide antigen and the specific neutralizing antibody and use thereof provided in the present disclosure, but they shall not be understood as limiting the protection scope of the present disclosure.

Example 1

Identification of the Broad-Spectrum Peptide Antigen of SARS-CoV-2 and the Antigen-Specific Detecting Method The amino acid sequence of the S2 protein of SARS-CoV-2 was analyzed with biological software, and potential antigenic peptide fragments were identified based on the hydrophilicity, antigenic index, surface site index and conservation of the S2 protein. A peptide with the amino acid sequence DPLQPELDSFKEELDKYFKNHT-SPDVDLGDIS (SEQ ID NO: 1) was obtained. Upon alignment, the peptide as set forth in SEQ ID NO: 1 shows no mutation in the S protein of SARS, SARS-CoV-2 of the genus 0-coronavirus and all SARS-CoV-2 variants discovered so far.

Example 2

I. Preparation of the ELISA Kit Using the Peptide Antigen

The peptide antigen in Example 1 was used to prepare the kit, which kit included:
  1. ELISA plate coated with peptide antigen.
  2. Enzyme-labeled antibody: horseradish peroxidase labeled mouse anti-human IgG.
  3. Substrate solution, prepared by steps as follows: 24.3 mL of 100 mmol/L citric acid solution (21 g citric acid was dissolved in deionized water, the volume was adjusted to 1 L) and 25.7 mL of 200 mmol/L $Na_2HPO_4·12H_2O$ (71.6 g $Na_2HPO_4·12H_2O$ was dissolved in deionized water, and the volume was adjusted to 1 L) were mix well, then 50 mg of tetramethylbenzidine (TMB) was added, and 50 μL of 30% $H_2O_2$ was added just before use.
  4. Stop solution: 2M $H_2SO_4$, prepared by mixing 89 mL of distilled water and 11 mL of concentrated $H_2SO_4$.
  5. Washing solution, prepared by adding 0.5 mL Tween-20 to 1000 mL of 10 mmol/L PBS (pH 7.4).
  6. Negative control (human negative serum) and positive control (inactivated human SARS-CoV-2-positive serum).

II. Preparation of the ELISA Plate of the Kit Coated with Peptide Antigen and Detection Method The obtained peptide was entrusted to Shanghai Dechi Biosciences Co., Ltd. to synthesize the peptide antigen, and the peptide antigen was coated following steps of the ELISA for detection of SARS-CoV-2 specific antibody, which specifically included steps:
  1. The peptide antigen was coated on the 96-well ELISA plate with a coating amount of 0.5 μg/well, a coating concentration of 5 μg/mL, and a total volume of 100 μL per well. After coating, each well was blocked overnight with PBST containing 1% fetal bovine serum and 5% skimmed milk powder;
  2. The serum to be tested was diluted at a ratio of 1:100 with PBST containing 5% skimmed milk powder and 1% fetal bovine serum, and added to the ELISA plate coated with peptide antigen for incubation;
  3. After the resulting mixture was washed several times, the horseradish peroxidase-labeled mouse anti-human secondary antibody was added for another incubation; the horseradish peroxidase-labeled mouse anti-human secondary antibody was diluted at a ratio of 1:40000 with PBST containing 5% skimmed milk powder and 1% fetal bovine serum;
  4. the resulting mixture was washed again for several times, and a TMB color developing solution was added for reaction;
  5. Finally, the reaction was terminated with sulfuric acid, and the OD value was read at a wavelength of 450 nm to detect the SARS-CoV-2 antibody level in the individual.

The sera to be tested were the inactivated sera of the COVID-19 recovered patients and the negative human serum. All the results in the examples were the average value of OD450 nm, and the results are shown in FIG. 1.

It was found by detecting the OD value using the ELISA kit that the peptide antigen reacted with 11 positive sera, but did not react with the remaining 8 negative sera, indicating that the peptide antigen could effectively recognize the antibody produced in the human against SARS-CoV-2.

Example 3

Method for Preparing the Fusion Protein Having Broad-Spectrum Triple Tandem Peptides 1) Design of primers for the amplification of the linearized vector pCold I and the 3 corresponding gene fragments containing SEQ ID NO: 1: the upstream primer for amplifying the linearized vector pCold I was located at position 337-361 of the plasmid pCold I; the downstream primer for amplifying the linearized vector pCold I was located at positions 295-318 of the plasmid pCold I. The amplified gene fragment containing SEQ ID NO: 1 was located at positions 3415-3510 of the SARS-CoV-2 S gene; the upstream primer for amplifying the first fragment has 15 bases reversely complementary to the downstream primer for amplifying the linearized vector pCold I at its 5'-end, and the reverse complement sequence of the corresponding bases encoding Linker GGGGS was added to the downstream primer; the corresponding base sequence encoding Linker GGGGS and its reverse complement sequence were added to the upstream and downstream primers for amplifying the second fragment, respectively; the downstream primer for amplifying the third fragment has 15 bases reversely complementary to the upstream primer for amplifying the linearized vector pCold I at its 5'-end, and the reverse complement sequence of the corresponding bases encoding Linker GGGGS was added to the downstream primer. The specific primer sequences, synthesized by Suzhou Jinweizhi Biotechnology Co., Ltd., are shown in Table 1.

TABLE 1

| Prime Sequences used during the generation of the fusion protein | | |
|---|---|---|
| PCR product | Primer sequence (5'-3') | Nos |
| The first fragment | F: atggagc tcggtaccga cccattgcaa cccgaacttg | SEQ ID NO: 2 |
| | R: acttcca cctccaccgc taatgtcgcc caggtccac | SEQ ID NO: 3 |
| The second fragment | F: ggtggag gtggaagtga cccattgcaa cccgaacttg | SEQ ID NO: 4 |
| | R: acttcca cctccaccgc taatgtcgcc caggtccac | SEQ ID NO: 3 |
| The third fragment | F: ggtggag gtggaagt g acccattgca acccgaactt g | SEQ ID NO: 4 |
| | R: caggtcg acaagctttc agctaatgtc gcccaggtcc ac | SEQ ID NO: 5 |
| Linearized vector pCold I | F: aagcttg tcgacctgca gtctagat | SEQ ID NO: 6 |
| | R: ggtaccg agctccatat gcctacc | SEQ ID NO: 7 |

Figure 3:
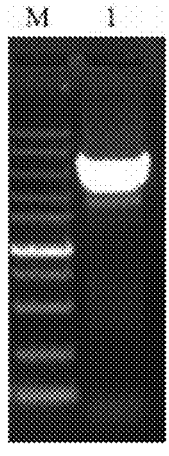
FIG. 3 is an electrophoresis diagram of the linearized vector pCold I amplified by PCR, in which lane 1 is the PCR product of the linearized vector pCold I; and lane M is DNA Marker.

2) PCR amplification of the linearized vector pCold I and 3 corresponding gene fragments containing SEQ ID NO: 1: plasmid pCold I and plasmid pcDNA3.1-SARS-CoV-2-S were used as templates respectively, and the primers in Table 1 were used as primers for PCR amplification. The PCR amplification reaction system included: 33 μl of water, 10 μl of 5× buffer, 1 μl of 10 mM dNTP, 2 μl of 10 μmol upstream primer, 2 μl of 10 μmol downstream primer, 1 μl of 10 ng/μl plasmid pCold I or plasmid pcDNA3.1-SARS-CoV-2-S (purchased from Shanghai HedgehogBio Science and Technology Co., Ltd.), and 1 μl of commercial Phanta Super-Fidelity DNA polymerase. The PCR amplification reaction parameters: denaturation at 94° C. for 5 minutes, followed by 30 cycles of denaturation at 94° C. for 30 seconds, annealing at 57° C. for 30 seconds, and extension at 72° C. for 3 minutes, and final extension at 72° C. for 10 minutes. After PCR, the PCR products were electrophoresed in a 1% agarose gel. As shown in FIG. 2, lane M is the DNA Marker, lane 1 is the PCR product of the first fragment, lane 2 is the PCR product of the second fragment, and lane 3 is the PCR product of the third fragment. As shown in FIG. 3, lane M is the DNA Marker and lane 1 is the PCR product of the linearized vector pCold I.

3) Rapid cloning of the three fragments into the vector pCold I: the purified linearized expression vector pCold I and three PCR products containing the corresponding gene fragment of SEQ ID NO: 1 were cloned using a commercial recombinase (ClonExpress® MultiS One Step Cloning Kit) for recombinant cloning. Reaction system: 2 μl of linearized vector (containing 100 ng), 1 μl each of the first fragment, the second fragment and the third fragment (each containing 10 ng), 4 μl of CE MultiS Buffer, 2 μl of Exnase MultiS, and 9 μl water. Reaction conditions: 37° C. for 30 minutes, then temperature decreased to 4° C. The recombinant product was then transformed into conventional DH5α competent bacteria and coated on LB plates. Bacterial clones were picked the next day for plasmid preparation, and positive clones were identified. Specifically, SEQ ID NO: 2 and SEQ ID NO: 5 were used as upstream and downstream primers for PCR identification of the picked clones. The reaction conditions and procedures were the same as in step 2).

4) Inducible expression and purification of the fusion protein with broad-spectrum triple tandem peptides: the obtained positive clones of transformed BL21 competent bacteria (named pCold I-3×P4) containing three corresponding gene fragments of SEQ ID NO: 1 were collected after induced by IPTG (0.1 mmol/ml) for ultrasonication (40 Hz). The sample treated by ultrasonication was centrifuged and separated as supernatant and pellet. SDS-PAGE (5% concentrated gel, 10% separating gel) and Western blot analysis (anti-P4 monoclonal antibody G5 as the primary antibody, HRP-labeled goat anti-mouse IgG as the secondary antibody) were used for the expression identification.

Figure 4:
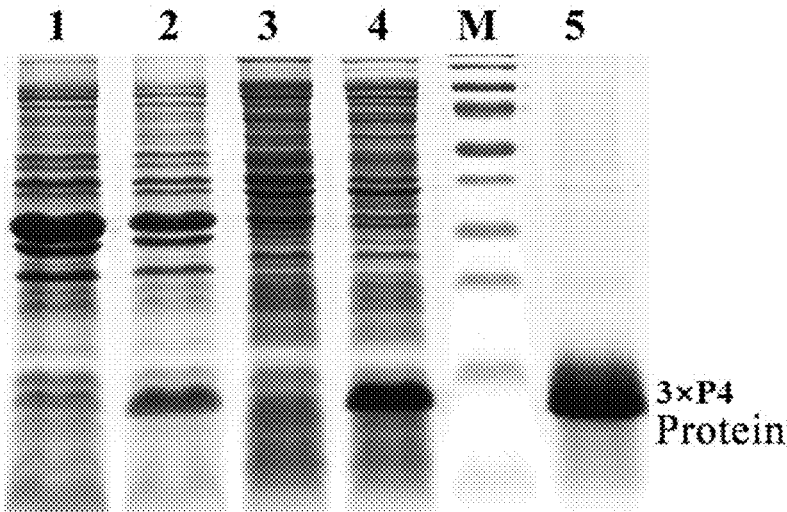
FIG. 4 shows the expression results of the fusion protein having broad-spectrum triple tandem peptides for SARS-CoV-2 as analyzed by SDS-PAGE, in which Lane 1 is the pellet of pCold I after ultrasonication; Lane 2 is the pellet of His-3×P4 after ultrasonication; Lane 3 is the supernatant of pCold I after ultrasonication; Lane 4 is the supernatant of His-3×P4 after ultrasonication; Lane 5 is the purified His-3×P4 protein; and Lane M is protein Marker.

In FIG. 4, the fusion protein having broad-spectrum triple tandem peptides, His-3×P4, could be expressed in a soluble form in the supernatant of the ultrasonicated sample. After the determination of the soluble expression of His-3×P4, the supernatant of the ultrasonicated sample was passed through a His purification column to purify the His-3×P4 protein. Lane 5 in FIG. 4 is the result for SDS-PAGE analysis of the purified His-3×P4 protein.

Figure 5:
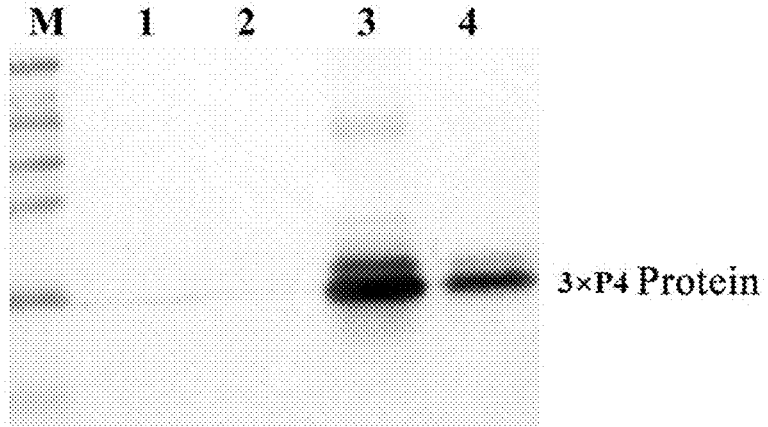
FIG. 5 shows the expression results of the fusion protein having broad-spectrum triple tandem peptides for SARS-CoV-2 identified by Western blot. Lane 1 is the pellet of pCold I after ultrasonication; Lane 2 is the supernatant of pCold I after ultrasonication; Lane 3 is the supernatant of His-3×P4 after ultrasonication; lane 4 is he pellet of His-3× P4 after ultrasonication; and lane M is protein Marker.

In FIG. 5, lane 4 is the Western blot analysis result of His-3×P4 protein after purification. The above results indicated that the fusion protein having broad-spectrum triple tandem peptides for SARS-CoV-2 could be efficiently expressed in the present disclosure, which may be promising in the serological diagnosis of SARS-CoV-2 and the development of broad-spectrum epitope vaccines.

Example 4

Method for Preparing the Broad-Spectrum Neutralizing Antibody to SARS-CoV-2

The fusion protein having broad-spectrum triple tandem peptides His-3×P4 was used as an immunogen to immunize mice to prepare the broad-spectrum anti-SARS-CoV-2 neutralizing antibody. Specifically, the method was as follows:

1) After His-3×P4 was mixed with Freund's complete adjuvant (the volume ratio of adjuvant to antigen was 1:1), the BALB/c mice were immunized for the first dose, and the dose for each immunization was 50 μg/mouse;

2) Fifteen days after immunization, His-3×P4 was mixed with Freund's incomplete adjuvant (the volume ratio of adjuvant to antigen was 1:1) and then the BALB/c mice were immunized for the second time, and the dose was 50 μg/mouse;

3) Twenty days after the second immunization, mouse serum was collected to obtain the broad-spectrum neutralizing antibody to SARS-CoV-2.

Example 5

Verification of the Broad-Spectrum Neutralizing Antibody to SARS-CoV-2

1. Detection method of the specificity of the broad-spectrum neutralizing antibody to SARS-CoV-2

Figure 6:
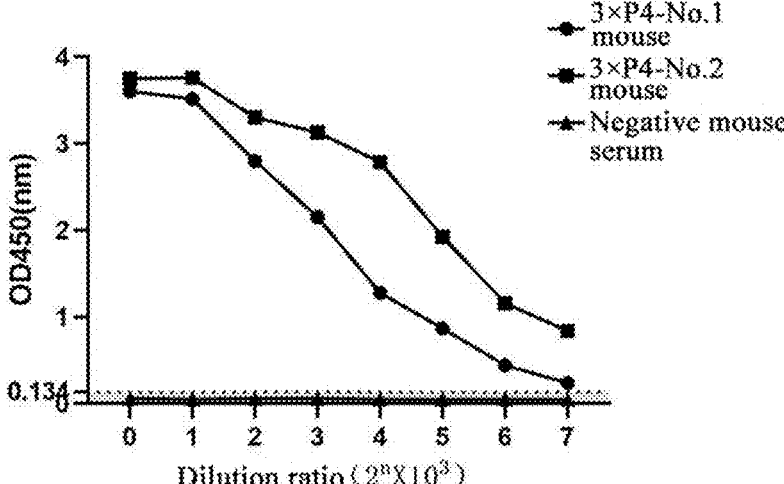
FIG. 6 shows the detection results of mouse sera against the fusion protein having broad-spectrum triple tandem peptides by ELISA using a coated peptide antigen.

1) The peptide antigen-coated ELISA plate prepared in Example 2 was used to detect the collected mouse serum;

2) The collected mouse sera were diluted and added to an ELISA plate coated with the peptide antigen for incubation;

3) After the resulting mixture was washed several times, the goat anti-mouse secondary antibody labeled with horseradish peroxidase was added for another incubation;

4) The resulting mixture was washed for several times, a TMB color developing solution was added for reaction;

5) Finally, the reaction was terminated with sulfuric acid, the OD value was read at a wavelength of 450 nm, and the anti-SARS-CoV-2 antibody level in the mouse was detected. The result is shown in FIG. 6.

2. Detection method for specific binding ability of the antigen and antibody

Figure 7:
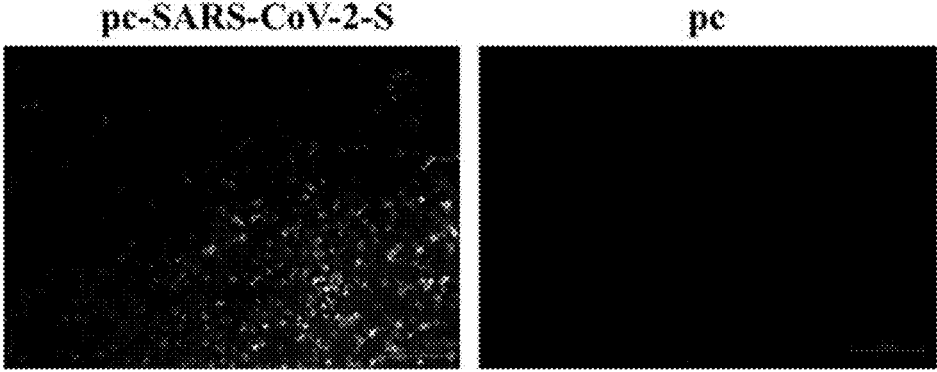
FIG. 7 shows the result of the reactivity between the mouse serum against fusion protein having broad-spectrum triple tandem peptides and SARS-CoV-2 S protein identified by an indirect immunofluorescence assay.

1) The eukaryotic expression plasmid pcDNA3.1-SARS-CoV-2-S expressing SARS-CoV-2 S protein was transfected into 293T cells;

2) Forty-eight hours after transfection, the cells were fixed with a acetone-ethanol fixative;

3) The collected mouse sera were diluted and incubated with the fixed cells;

4) After the resulting mixture was washed several times, FITC-labeled goat anti-mouse secondary antibody was added for another incubation;

5) The resulting mixture was observed under an inverted fluorescence microscope, and the result is shown in FIG. 7.

3. Detection method for neutralizing specificity of the antibody

Figure 8:
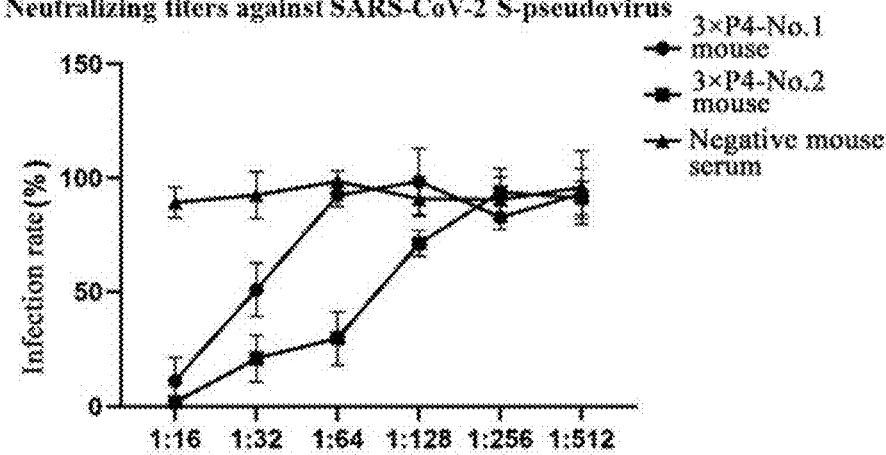
FIG. 8 shows the result for the neutralizing activity of the anti-fusion protein having broad-spectrum triple tandem peptides mouse sera by SASR-CoV-2 S-pseudovirus neutralization assay.

1) The collected mouse sera were gradually diluted and co-incubated with the same amount of S protein of SARS-CoV-2 pseudovirus (containing the GFP-Luciferase reporter gene);

2) The incubated antibody-pseudovirus mixture was added into 293T cells stably expressing human ACE2;

3) After 8 hours, the cell culture supernatant was discarded, and fresh culture medium was added for continuous culture;

4) Sixty hours after the virus infection, the Luciferase reporter assay kit was used to detect the Luciferase fluorescence intensity of the cells, the infection rate of the virus was calculated according to formula I, and the result is shown in FIG. 8;

Virus infection rate (%)=(Luciferase fluorescence intensity of the serogroup/Luciferase fluorescence intensity of the PBS group)×100%          Formula I.

The above three experiments showed that the broad-spectrum SARS-CoV-2 antibody prepared in the present disclosure could not only effectively recognize the SARS-CoV-2 S protein, but also effectively neutralize the S protein of SARS-CoV-2 of the pseudovirus and inhibit virus from invading the 293T cells stably expressing human ACE2. The above results indicated that the broad-spectrum neutralizing antibody to SARS-CoV-2 prepared in the present disclosure had a good effect and was promising in anti-infective treatment, vaccine development and detection kit development of SARS-CoV-2.

The description of the above embodiments is only used to help understand the method and core idea of the present disclosure. It should be pointed out that for those of ordinary skill in the art, without departing from the principle of the present invention, several improvements and modifications can be made to the present disclosure, and these improvements and modifications also fall within the protection scope of the claims of the present disclosure. Various modifications to these embodiments are obvious to those skilled in the art, and the general principles defined herein can be implemented in other embodiments without departing from the spirit or scope of the present invention. Therefore, the present disclosure will not be limited to the embodiments shown in this document, but claims the widest scope consistent with the principles and novel features disclosed in this document.

---

What is claimed is:

1. A fusion protein having broad-spectrum triple tandem peptides for SARS-COV-2, wherein the fusion protein comprises three tandemly arranged sequences of a broad-spectrum peptide antigen of SARS-COV-2, and the broad-spectrum peptide antigen comprises the amino acid sequence of SEQ ID NO: 1, and wherein the fusion protein comprises the amino acid sequence of SEQ ID NO: 8.

* * * * *

SEQUENCE LISTING

<160> NUMBER OF SEQ ID NOS: 9

<210> SEQ ID NO 1
<211> LENGTH: 32
<212> TYPE: PRT
<213> ORGANISM: Artificial Sequence
<220> FEATURE:
<223> OTHER INFORMATION: Amino acid sequence of the broad-spectrum
      peptide antigen

<400> SEQUENCE: 1

-continued

```
Asp Pro Leu Gln Pro Glu Leu Asp Ser Phe Lys Glu Glu Leu Asp Lys
1               5                   10                  15

Tyr Phe Lys Asn His Thr Ser Pro Asp Val Asp Leu Gly Asp Ile Ser
            20                  25                  30

<210> SEQ ID NO 2
<211> LENGTH: 37
<212> TYPE: DNA
<213> ORGANISM: Artificial Sequence
<220> FEATURE:
<223> OTHER INFORMATION: Upstream primer of the first fragment

<400> SEQUENCE: 2
atggagctcg gtaccgaccc attgcaaccc gaacttg                            37

<210> SEQ ID NO 3
<211> LENGTH: 36
<212> TYPE: DNA
<213> ORGANISM: Artificial Sequence
<220> FEATURE:
<223> OTHER INFORMATION: Downstream primer of the first fragment and the
      second fragment

<400> SEQUENCE: 3
acttccacct ccaccgctaa tgtcgcccag gtccac                             36

<210> SEQ ID NO 4
<211> LENGTH: 37
<212> TYPE: DNA
<213> ORGANISM: Artificial Sequence
<220> FEATURE:
<223> OTHER INFORMATION: Upstream primer of the second fragment and the
      third fragment

<400> SEQUENCE: 4
ggtggaggtg gaagtgaccc attgcaaccc gaacttg                            37

<210> SEQ ID NO 5
<211> LENGTH: 39
<212> TYPE: DNA
<213> ORGANISM: Artificial Sequence
<220> FEATURE:
<223> OTHER INFORMATION: Downstream primer of the third fragment

<400> SEQUENCE: 5
caggtcgaca agctttcagc taatgtcgcc caggtccac                          39

<210> SEQ ID NO 6
<211> LENGTH: 25
<212> TYPE: DNA
<213> ORGANISM: Artificial Sequence
<220> FEATURE:
<223> OTHER INFORMATION: Upstream primer of the linearized pcold I
      vector

<400> SEQUENCE: 6
aagcttgtcg acctgcagtc tagat                                         25

<210> SEQ ID NO 7
<211> LENGTH: 24
<212> TYPE: DNA
<213> ORGANISM: Artificial Sequence
<220> FEATURE:
<223> OTHER INFORMATION: Downstream primer of the linearized pcold I
      vector
```

-continued

```
<400> SEQUENCE: 7
ggtaccgagc tccatatgcc tacc                                                 24

<210> SEQ ID NO 8
<211> LENGTH: 130
<212> TYPE: PRT
<213> ORGANISM: Artificial Sequence
<220> FEATURE:
<223> OTHER INFORMATION: Amino acid sequence of the fusion protein

<400> SEQUENCE: 8

His His His His His His Ile Glu Gly Arg His Met Glu Leu Gly Thr
1               5                   10                  15

Asp Pro Leu Gln Pro Glu Leu Asp Ser Phe Lys Glu Glu Leu Asp Lys
            20                  25                  30

Tyr Phe Lys Asn His Thr Ser Pro Asp Val Asp Leu Gly Asp Ile Ser
            35                  40                  45

Gly Gly Gly Gly Ser Asp Pro Leu Gln Pro Glu Leu Asp Ser Phe Lys
    50                  55                  60

Glu Glu Leu Asp Lys Tyr Phe Lys Asn His Thr Ser Pro Asp Val Asp
65                  70                  75                  80

Leu Gly Asp Ile Ser Gly Gly Gly Gly Ser Asp Pro Leu Gln Pro Glu
            85                  90                  95

Leu Asp Ser Phe Lys Glu Glu Leu Asp Lys Tyr Phe Lys Asn His Thr
            100                 105                 110

Ser Pro Asp Val Asp Leu Gly Asp Ile Ser Lys Leu Val Asp Leu Gln
        115                 120                 125

Ser Arg
    130

<210> SEQ ID NO 9
<211> LENGTH: 5
<212> TYPE: PRT
<213> ORGANISM: Artificial Sequence
<220> FEATURE:
<223> OTHER INFORMATION: Amico acid sequence of the connecting peptide

<400> SEQUENCE: 9

Gly Gly Gly Gly Ser
1               5
```